United States Patent [19]

Akhavi

[11] 4,385,637
[45] May 31, 1983

[54] BLOOD SAMPLER

[75] Inventor: David S. Akhavi, Los Angeles, Calif.

[73] Assignee: American Hospital Supply Corporation, Evanston, Ill.

[21] Appl. No.: 220,576

[22] Filed: Dec. 29, 1980

Related U.S. Application Data

[62] Division of Ser. No. 25,980, Apr. 2, 1979, Pat. No. 4,266,559.

[51] Int. Cl.³ ............................................. A61B 5/14
[52] U.S. Cl. ................................... 128/763; 128/767; 73/863.23; 210/927
[58] Field of Search ................................ 128/763–771, 128/215, 216, 218 N; 210/927, DIG. 24; 604/214, 126, 168; 73/863.23, 864.14–864.15

[56] References Cited

U.S. PATENT DOCUMENTS

| | | | |
|---|---|---|---|
| 3,136,440 | 6/1964 | Krug et al. | 128/764 X |
| 3,157,481 | 11/1964 | Bujan | 55/417 |
| 3,304,934 | 2/1967 | Bautista | 128/764 X |
| 3,344,786 | 10/1967 | Berg et al. | 128/215 |
| 3,693,407 | 9/1972 | McWhorter et al. | 128/760 X |
| 3,962,085 | 6/1976 | Liston et al. | 210/927 X |
| 4,046,144 | 9/1977 | McFarlane | 128/214.4 |
| 4,133,304 | 1/1979 | Bailey | 128/764 |
| 4,200,096 | 4/1980 | Charvin | 128/214.4 |
| 4,215,701 | 8/1980 | Raitto | 128/763 |

Primary Examiner—Lee S. Cohen
Assistant Examiner—Angela D. Sykes
Attorney, Agent, or Firm—Roger A. Williams

[57] ABSTRACT

A device particularly suited for collecting and dispensing an arterial blood sample. A needle is connected to a flexible transparent tube that includes an air exit vent with a nonwet filter so air, but not blood, can exit the vent under arterial blood pressure. A special needle adapter prevents formation of air bubbles, and a baffle system in the needle minimizes blood and air mixing. A clamp on the reservoir pinches off an air contaminated blood segment and can longitudinally strip a different blood segment which is not air contaminated. The tubular reservoir has an oxygen blocking coating, and its internal surface includes a dry anticoagulant coating.

14 Claims, 8 Drawing Figures

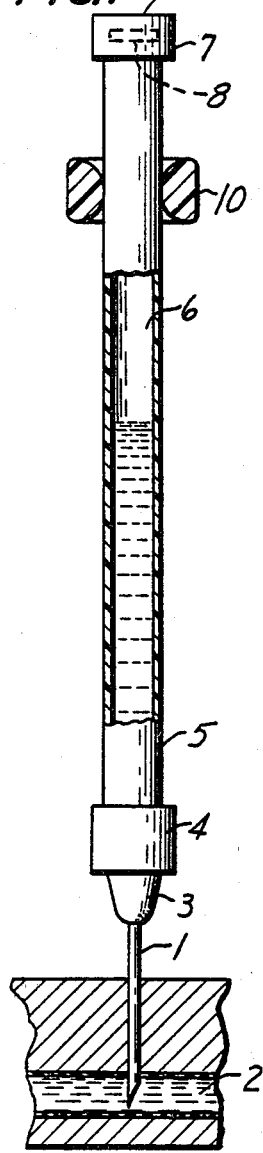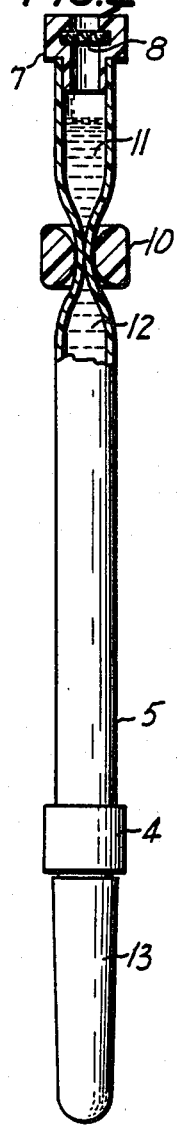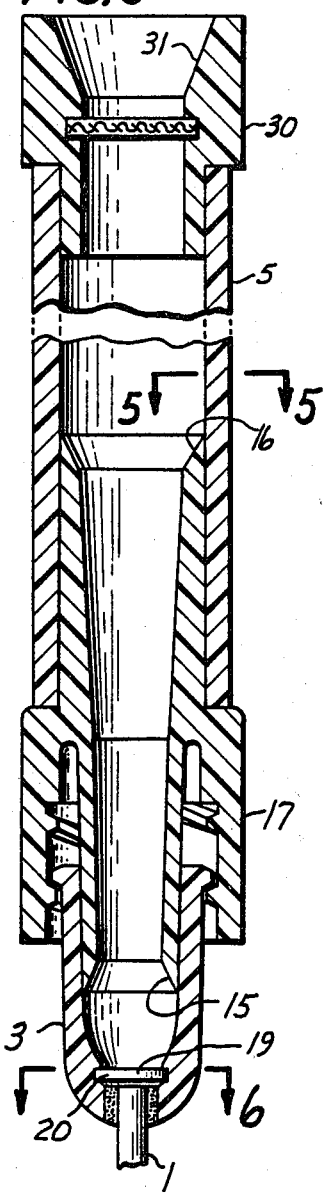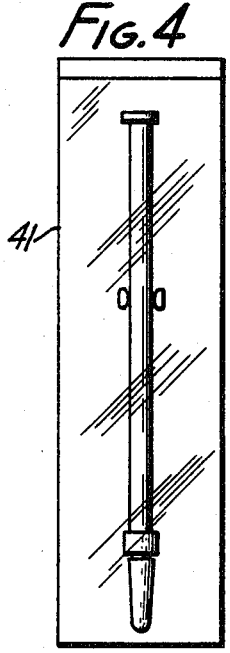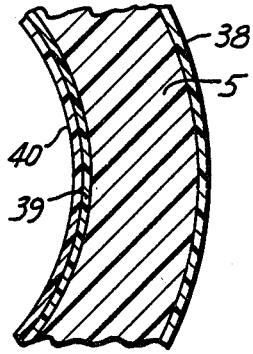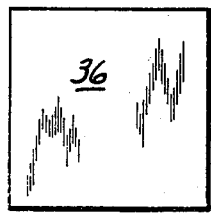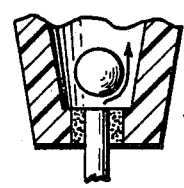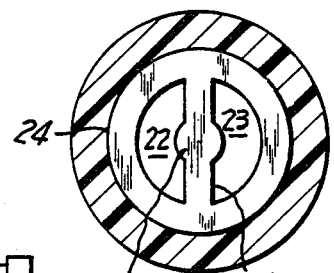

BLOOD SAMPLER

This application is a division, of application Ser. No. 025,980, filed Apr. 2, 1979, now U.S. Pat. No. 4,266,559.

BACKGROUND

Venous blood has long been collected for various medical tests. Recently, it has become more important to also collect arterial blood for measuring of the partial pressures of dissolved oxygen and carbon dioxide in the arterial system.

When collecting a blood sample, it is important to distinguish at the time of collection whether it is arterial or venous blood. In the past, arterial blood has been detected by use of glass syringes in which the arterial blood pressure would be sufficient to force back the syringe plunger; venous pressure would not. U.S. Pat. No. 3,930,429 also proposes a plastic syringe system for distinguishing arterial pressure. However with plunger type arterial blood collectors, these plungers can sometimes catch and drag, making it difficult to clearly distinguish that the blood is arterial.

Recently, others have proposed the use of a glass tube connected to a needle, thereby eliminating the plunger. Such device required the use of a manually applied cork to plug the rear end of the glass tube to prevent the blood sample from spilling out. Because the glass tube was rigid, it was also difficult to dispense the blood sample into a machine that did not have a vacuum extractor for the blood sample. Because it did not have a plunger, such sample could not be forced into the machine.

Additional problems with prior arterial blood samplers have included transmission of oxygen through the sampler's wall to cause erroneous readings on the blood, and liquid heparin in the sampler which introduced an error into the readings for oxygen and carbon dioxide. These problems are described in the following publications:

Scott et al., "Leakage of Oxygen From Blood and Water Samples Stored in Plastic and Glass Syringes," *British Medical Journal*, Aug. 28, 1971, 3, pp. 512-516.

Hansen et al., "A Systematic Error in the Determination of Blood $P_{CO_2}$," *American Review of Respiratory Disease*, Vol. 115, 1977, pp. 1061-1063.

Hamilton et al., "Arterial Blood Gas Analysis: Potential Errors Due to Addition of Heparin," *Anaesthesia and Intensive Care*, Vol. VI, No. 3, August 1978, pp. 251-255.

SUMMARY OF THE INVENTION

The present invention overcomes the problems described above and includes a blood sampler with a needle connected to a flexible reservoir tube having a vent closed by a valve structure which permits the expulsion of gas from the reservoir, but not blood. A needle adapter with a special beveled construction prevents the formation of air bubbles during collection of a blood sample, and a baffle structure in the needle prevents turbulent mixing of blood and its overriding air as the blood fills the reservoir. A clamp on the flexible tube segments the collected sample into an air contaminated segment and a test segment, and this clamp can strip the collected blood sample from the reservoir into a testing machine that does not have a vacuum sample extractor. The flexible tube has a gas blocking coating to prevent transmission of oxygen or carbon dioxide through the tube's wall. The tube also has an internal coating of dry anticoagulant.

THE DRAWINGS

FIG. 1 is a front elevational view of the blood sampler partially filled with the blood sample;

FIG. 2 is a view similar to FIG. 1 with the sampler filled with the blood sample;

FIG. 3 is an enlarged sectional view of the needle adapter and showing an alternate form of the vent structure;

FIG. 4 is a view of the packaged sampler;

FIG. 5 is an enlarged view taken along line 5—5 of FIG. 3;

FIG. 6 is an enlarged view of the first baffle structure taken along line 6—6 of FIG. 3;

FIG. 7 is a view of the sampler connected with the testing machine.

FIG. 8 is a fragmentary view showing a second baffle structure in the form of a ball.

DETAILED DESCRIPTION

In FIG. 1, a needle including a cannula 1 is shown inserted into a patient to tap arterial blood 2. The needle includes a hub 3 which is attached by means of a needle adapter 4 to a transparent flexible plastic tube 5 forming a blood collection reservoir. This plastic tube 5 can be of a thermoplastic or thermoset material which has elastomeric or rubber like properties so it can be pinched shut and reopened upon removal of the pinching forces. In FIG. 1, blood is shown welling up in the reservoir tube by means of arterial blood pressure and forcing the overriding air 6 out through a vent 7. Vent 7 includes a one-way valve structure 8 in the form of a "nonwet" filter. Such filter will permit the passage of gas, such as sterile air, from the reservoir, but will not permit the passage of blood.

The details of a first embodiment of the vent and nonwet filter structure of FIG. 1 is shown in detail in FIG. 2. In FIG. 2, the complete blood sample has been collected and a clamp 10 has been positioned along the reservoir 5 and the flexible tube is pinched shut by clamp 10 to segregate the collected blood sample into an air contaminated segment 11 and a test segment 12. Thus, any change in the oxygen or carbon dioxide partial pressure of the blood caused by its contact with air is minimized by segmenting sample 11 from the test machine. With a blood sampler, it is customary to stick the needle into a rubber plug (not shown) to prevent leakage. If desired, the rubber plug could be inside a needle protector 13. An alternative way of containing the sample is to remove the needle and place a syringe cap (not shown) on a tip of the syringe.

As previously mentioned, it is important to minimize the turbulent contact with the blood sample and air, particularly when the sample taken is arterial blood in which the partial pressure of oxygen and carbon dioxide are to be measured. In FIG. 3, the needle adapter has a special structure for minimizing air bubble hangups when collecting the sample. The needle adapter 4 has a tubular structure with an internally beveled lower end 15 and an internally beveled upper end 16. Tests have shown that such structure causes the blood sample to smoothly well up in the collecting reservoir. For instance, when end 15 was at 90° to the longitudinal axis of the adapter, air bubbles continuously formed at such intersection of the needle adapter and hub 3.

The needle hub 3 is firmly held to the needle adapter by an internally threaded collar 17. The needle hub also includes a structure which prevents the turbulent mixing of the blood sample and air, particularly during an inrush of arterial blood. The needle hub of FIG. 3 is shown with a first baffle structure 19 that can be snap fitted into an undercut groove 20 in the hub, or press fitted into a hub without undercut, or otherwise secured to the hub. Preferably, the baffle structure as shown in FIG. 6 has one or more openings, such as 22 and 23, which combine to form a passage at least as large as an internal diameter of cannula 1. By such large passage to the baffle structure, the inflow of blood from an arterial source is not sufficiently slowed down so as to be confused with venous blood under a much lower pressure. The baffle system is not intended to be a high pressure drop filtering system which might so restrict the flow of blood that it would take an inordinate amount of time to collect the sample.

The baffle of FIG. 6 includes a peripheral ring 24 which is bridged by a central bar 25. If desired for molding purposes, an enlarged central section 26 can be added for a mold gate. An alternative form of a baffle, shown in FIG. 8, is a ball in the needle that can prevent turbulent blood and air mixing and yet does not interfere with the flow rate distinction between arterial and venous blood.

In the second embodiment of the vent structure shown at 30 of FIG. 3, an internally tapered extension 31 is provided. Extension 31 can receive a hypodermic syringe if it is desired not to use the clamp 10, but to force the blood sample out of the reservoir into the testing machine. Such extension 31 could also be used with a syringe to apply a vacuum to the reservoir for collecting slow flowing venous or arterial blood.

Once the blood sample has been collected, the protector and needle can be removed and the needle adapter joined directly to a testing machine 36 to measure the partial pressure of oxygen and carbon dioxide in the arterial blood sample. Most such testing machines include a very small tubular probe that fits inside the reservoir and sucks out a measured amount of blood for the test.

In some machines that do not have such an automatic vacuum extractor, a clamp can be used to manually strip the blood sample into the machine. This can be done either by sliding a clamp, such as schematically shown at 10, along the tube. Alternatively, a roller type clamp, such as schematically shown at 37, could be used to roll along the flexible tube reservoir. When a clamp such as 10 is used for sliding, it is preferable to coat the outer surface of the tube or internal surface of the clamp with a lubricant, such as silicone or a teflon coating shown at 38 in FIG. 5.

It has been found that a reservoir 5 of polyurethane remains flexible and highly squeezable even when subjected to ice bath storage at 0° C. This flexibility is useful in expelling the sample and also rolling the tube in the hands to remix any separated plasma and hemoglobin prior to testing. Such rolling feature also helps to mix the blood with an anticoagulant. Another material that remains flexible and squeezable is a blank copolymer, marketed under the trademark KRATON, by Shell Chemical Company. However, KRATON does not work as well as polyurethane because of its more limited transparency and more tacky external surface making it more difficult to slide a clamp, such as clamp 10. Preferably, the tubular reservoir has a Shore A hardness of 40 to 100.

As mentioned in the publications above, it is highly critical to minimize any transmission of oxygen or carbon dioxide across the reservoir wall 5. Because polyurethane is somewhat pervious to oxygen and carbon dioxide, an internal gas blocking barrier coating or layer 39 is applied to the inner surface of the polyurethane reservoir. This blocking coating which prevents transmission of oxygen and carbon dioxide can be a copolymer of vinylidene chloride and acrylonitrile, which is also known under the trademark SARAN.

This gas blocking coating is further covered with a dry anticoagulant 40, such as heparin. Because the heparin is in dry form, it has very little geometric volume to substantially change the partial pressure of oxygen or carbon dioxide in the blood to cause errors.

FIG. 4 shows the blood sampler in a package 41 which preferably maintains the sampler in sterile condition until ready to use. The package can then be opened and the sampler is extremely useful for collecting and dispensing an arterial blood sample. However, it can also be useful in collecting a venous blood sample, but the inflow of blood would be much slower unless a vacuum were applied by syringe to the FIG. 3 embodiment.

The blood collecting reservoir can have an internal diameter of 0.100 to 0.300 inch, a wall thickness of 0.010 to 0.100 inch, and a length of 2 to 12 inches for an adult blood sample. A smaller diameter tube could be used for collecting a blood sample from an infant.

In the above description, specific examples have been used to describe the invention. However, it is understood by those skilled in the art that certain modifications can be made to these examples without departing from the spirit and scope of the invention.

I claim:

1. An arterial blood sampler comprising: a needle; a blood reservoir connected to the needle and having a gas therein, said reservoir being of a material pervious to blood gas; a coating on the reservoir that is substantially impervious to blood gas to reduce air in laboratory tests on collected blood; a vent on the reservoir through which gas can be expelled by means of arterial blood pressure; and valve means on the vent preventing the escape of arterial blood from the reservoir.

2. An arterial blood sampler as set forth in claim 1 wherein the reservoir comprises a material sufficiently flexible at 0° to be readily compressed to expel blood immediately after removal of the sampler from an ice bath.

3. An arterial blood sampler as set forth in claim 1, wherein the reservoir is of polyurethane.

4. An arterial blood sampler as set forth in claim 1, wherein said coating is on at least one surface of the reservoir, said coating being a copolymer of vinylidene chloride and acrylonitrile.

5. An arterial blood sampler as set forth in claim 4, where said copolymer coating is only on the inner surface of the reservoir.

6. An arterial blood sampler comprising: a needle having a hollow hub; a flexible plastic blood reservoir connected to a needle adapter having a tubular section that extends inside both the reservoir and the hollow hub of the needle, and the tubular section of the adapter has internally beveled ends so as to reduce turbulence of blood flow into the sampler; a coating on the reservoir that is substantially impervious to blood gas; and gas within the blood reservoir; a vent on the reservoir through which such gas can be expelled by means of arterial blood pressure; and valve means on the vent preventing the escape of arterial blood from the reservoir.

7. An arterial blood sampler as set forth in claim 6, wherein the needle adapter has a threaded collar securing the needle to the adapter.

8. A blood sampler comprising: a needle; a flexible plastic reservoir of a material pervious to blood gas; and a blocking coating on at least one surface of the reservoir, which blocking coating is substantially impervious to blood gas transfer.

9. A blood sampler as set forth in claim 8, wherein the reservoir is of polyurethane, and the blocking coating is of a copolymer of vinylidene chloride and acrylonitrile.

10. A blood sampler as set forth in claim 9, wherein the coated reservoir has a Shore hardness of from 40 to 100.

11. A blood sampler comprising: a needle having a hub; a baffle within the needle hub; and a blood reservoir connected to the needle hub wherein the baffle includes a peripheral ring and a transverse bar diametrically joining opposite sides of the ring, which baffle can disperse incoming blood without substantially slowing blood flow.

12. A blood sampler as set forth in claim 11, wherein the needle has a cannula and the baffle has one or more openings that combine to form a passage at least as large as the cannula so as not to substantially restrict blood flow.

13. A needle comprising: a hub; a cannula attached to the hub; and a baffle in the hub, said baffle having one or more openings that combine to form a passage at least as large as the cannula's internal diameter so as not to substantially restrict blood flow and wherein the baffle includes a peripheral ring and a transverse bar diametrically joining opposite sides of the ring.

14. A needle as set forth in claim 13, wherein the hub has an internal groove retaining the baffle.

* * * * *

UNITED STATES PATENT AND TRADEMARK OFFICE
CERTIFICATE OF CORRECTION

PATENT NO. : 4,385,637
DATED : May 31, 1983
INVENTOR(S) : David S. Akhavi

It is certified that error appears in the above-identified patent and that said Letters Patent are hereby corrected as shown below:

Column 4, line 52, change "1" to -- 2 --.

Column 4, line 54, change "1" to -- 2 --.

Column 4, line 68, change "and" to -- a --.

Signed and Sealed this

Sixth Day of September 1983

[SEAL]

Attest:

GERALD J. MOSSINGHOFF

Attesting Officer

Commissioner of Patents and Trademarks